(12) United States Patent
Higashiyama et al.

(10) Patent No.: US 8,841,097 B2
(45) Date of Patent: *Sep. 23, 2014

(54) PROCESS FOR PRODUCING UNSATURATED FATTY ACID-CONTAINING OILS

(75) Inventors: Kenichi Higashiyama, Mishima-gun (JP); Kengo Akimoto, Mishima-gun (JP); Sakayu Shimizu, Kyoto (JP)

(73) Assignee: Suntory Holdings Limited, Osaka-shi, Osaka (JP)

( * ) Notice: Subject to any disclaimer, the term of this patent is extended or adjusted under 35 U.S.C. 154(b) by 1664 days.

This patent is subject to a terminal disclaimer.

(21) Appl. No.: 11/407,984

(22) Filed: Apr. 21, 2006

(65) Prior Publication Data

US 2006/0189588 A1    Aug. 24, 2006

Related U.S. Application Data

(63) Continuation of application No. 09/254,152, filed as application No. PCT/JP97/02989 on Aug. 27, 1997, now Pat. No. 7,091,244.

(30) Foreign Application Priority Data

Aug. 30, 1996 (JP) ..................................... 8-230210

(51) Int. Cl.
| | |
|---|---|
| C12P 7/64 | (2006.01) |
| A61K 31/20 | (2006.01) |
| C07C 53/00 | (2006.01) |
| A23L 1/30 | (2006.01) |
| A23D 9/00 | (2006.01) |
| A23K 1/16 | (2006.01) |
| A23L 1/29 | (2006.01) |

(52) U.S. Cl.
CPC ............ *C12P 7/6472* (2013.01); *A23L 1/3008* (2013.01); *A23V 2002/00* (2013.01); *Y10S 426/801* (2013.01); *Y10S 426/807* (2013.01); *A23D 9/00* (2013.01); *A23K 1/164* (2013.01); *A23L 1/296* (2013.01)
USPC ............... 435/134; 514/560; 514/546; 554/1; 426/801; 426/807

(58) Field of Classification Search
USPC .................. 514/560, 546; 435/134; 554/1
See application file for complete search history.

(56) References Cited

U.S. PATENT DOCUMENTS

| | | | |
|---|---|---|---|
| 5,093,249 A | 3/1992 | Nakajima et al. | |
| 5,322,780 A | 6/1994 | Kawashima et al. | .......... 435/134 |
| 5,583,019 A | 12/1996 | Barclay | .......... 435/134 |
| 6,117,905 A | 9/2000 | Higashiyama et al. | |
| 6,280,982 B1 | 8/2001 | Kawashima | |
| 6,602,690 B2 | 8/2003 | Kawashima | |

FOREIGN PATENT DOCUMENTS

| | | |
|---|---|---|
| EP | 155 420 A1 | 9/1985 |
| EP | 0223960 A2 | 6/1987 |
| EP | 0269351 A2 | 6/1988 |
| EP | 0276541 A2 | 8/1988 |
| EP | 0522470 A1 | 1/1993 |
| EP | 0535940 | 4/1993 |
| EP | 0726321 A2 | 8/1996 |
| EP | 0252716 A2 | 1/1998 |
| EP | 0 957 173 | 9/2004 |
| JP | 63-044891 | 2/1988 |
| JP | A-63-133994 | 6/1988 |
| JP | 64-38007 | 2/1989 |
| JP | A-1-215245 | 9/1989 |
| JP | 1-304892 A | 12/1989 |
| JP | A-3-72892 | 3/1991 |
| JP | A-5-17796 | 1/1993 |
| JP | 5-091887 | 4/1993 |
| JP | A-5-308979 | 11/1993 |
| JP | A-7-59540 | 3/1995 |
| WO | 92/13086 A1 | 8/1992 |
| WO | 94/28913 | 12/1994 |
| WO | 96/21037 | 7/1996 |
| WO | 97/37032 | 10/1997 |
| WO | 97/43362 | 11/1997 |

OTHER PUBLICATIONS

Huang et al., "Arachidonate and Docosahexaenoate Added to Infant Formula Influence Fatty Acid Composition and Subsequent Eicosanoid Production in Neonatal Pigs," J. Nutr., vol. 126, 1996, pp. 2199-2208.

Office Action issued by Korean Patent Office in Korean application No. 10-2008-7015951 issued Aug. 18, 2008 (with English-language translation).

Shimizu et al., "Production of Eicosapentaenoic Acid by *Mortierella* Fungi," *JAOCS* 65(9): 1455-1459 (1988).

Bajpai et al., "Production of arachidonic acid by *Mortierella* alpine ATCC 32222," *J. Ind. Microbiology* 8: 179-185 (1991).

Bajpai et al., "Effects of Aging *Mortierella* Mycelium on Production of Arachidonic and Eicosapentaenoic Acids," *JAPCS* 68(10): 775-780 (1991).

Lindberg et al., "Effect of temperature and glucose supply on the production of polyunsaturated fatty acid by the fungus *Mortierella* alpine CBS 343.66 in fermentor cultures," *Appl. Microbiol. Biotech.* 39: 450-455 (1993).

(Continued)

*Primary Examiner* — Shengjun Wang

(74) *Attorney, Agent, or Firm* — Drinker Biddle & Reath LLP

(57) ABSTRACT

An edible oil obtained by culturing a microorganism belong to the genus *Mortierella* subgenus *Mortierella* in a medium containing a nitrogen source derived from soybean is discussed. The oils obtained have a low 24,25-methylenecholest-5-en-3β-ol content.

6 Claims, No Drawings

(56) References Cited

OTHER PUBLICATIONS

Totani et al., "A simple method for production of arachidonic acid by *Mortierella alpina*," *Appl. Microbiol. Biotech.* 28: 135-137 (1988).
Boswell et al., "Preclinical Evaluation of Single-cell Oils that are Highly Enriched with Arachidonic Acid and Docosahexaenoic Acid," *Food Chem. Toxicology* 34: 585-593 (1995).
Declaration of Angela Tsetsis submitted in opposition to EP 0 957 173 B1 Jun. 22, 2005.
Declaration of Chris Lindsay submitted in opposition to EP 0 957 173 B1 Jun. 22, 2005.
Declaration of Sandy Diltz submitted in opposition to EP 0 957 173 B1 Jun. 22, 2005.
First declaration of Dr Fujikawa submitted in opposition to EP 0 957 173 B1 Sep. 5, 2006.
Declaration of Kenji Katano submitted in opposition to EP 0 957 173 B1 Sep. 5, 2006.
Exhibit entitled "D23: Sixteen invoices and 'Packing Slip' documents in respect of A017-40-DS oil with dates in the period from Apr. 19, 1996 to Aug. 23, 1996," submitted in opposition to EP 0 957 173 B1 Dec. 21, 2007.
Second Declaration by Angela Tsetsis including two Annexes submitted in opposition to EP 0 957 173 B1.
Exhibit entitled "D25: Nutricia press release," submitted in opposition to EP 0 957 173 B1 Dec. 21, 2007.
Exhibit entitled "D26: Certificate of analysis for A017-40-DS," submitted in opposition to EP 0 957 173 B1 Dec. 21, 2007.
Second Declaration by Chris Lindsay submitted in opposition to EP 0 957 173 B1 Dec. 21, 2007.
Exhibit entitled "D28: Two invoices in respect of sales of AO11-DS oil," submitted in opposition to EP 0 957 173 B1 Dec. 21, 2007.
Second Declaration of Sandy Diltz submitted in opposition to EP 0 957 173 B1 Dec. 21, 2007.
Exhibit entitled "D30: Two invoices in respect of sales of A013-DS oil," submitted in opposition to EP 0 957 173 B1 Dec. 21, 2007.
Exhibit entitled "D31: Text of email from publishers of Boswell et al, Food Chem. Toxicology 34 (1995) 585-593," submitted in opposition to EP 0 957 173 B1 Dec. 21, 2007.
Description of Opponent I fermentation experiments submitted in opposition to EP 0 957 173 B1 Dec. 21, 2007.
Exhibit entitled "D32(8): Peak assignment of 24,25-methylenecholest-5-en-3β-01 (24,25-M) and ergosta-5,25-dien-3b-ol (ergosta-5,25) by GC-MS," submitted in opposition to EP 0 957 173 B1 Jul. 3, 2008.
Label from Arasco A017-40-DS submitted in opposition to EP 0 957 173 B1 Dec. 21, 2007.
Analysis of Arasco A017-40DS submitted in opposition to EP 0 957 173 B1 Dec. 21, 2007.
Declaration of Dr J. H. Wolf submitted in opposition to EP 0 957 173 B1 Dec. 21, 2007.
Declaration of Dr. A. Carvalho De Souza submitted in opposition to EP 0 957 173 B1 Dec. 21, 2007.
Li et al., *Can. J. Chem. Eng.* 73: 135-139 (1995).
Exhibit entitled "D24a: Product information on Sigma S9633 soy flour," submitted in opposition to EP 0 957 173 B1 Dec. 21, 2007.
Exhibit entitled "D25a: Product information on soy flour from Cargill," submitted in opposition to EP 0 957 173 B1 Dec. 21, 2007.
Second declaration of Dr. Fujikawa submitted in opposition to EP 0 957 173 B1 Feb. 13, 2008.
Declaration of Dr. Higashiyama submitted in opposition to EP 0 957 173 B1 Feb. 13, 2008.
Exhibit entitled "D41: Extracts from Fungal Nutrition and Physiology, Michael Garraway and Robert Evans, Wiley 1984," submitted in opposition to EP 0 957 173 B1 Nov. 30, 2008. (Fungal Nutrition and Physiology, Michael Garraway and Robert Evans, eds., Wiley, New York, pp. 172-173, 193-195, 1984.).
Exhibit entitled "D42: Fermentation of *M. alpina* ATCC32222 using the protocol as described in Example 7 of WO 96/21037 and analysis of oil obtained therefrom (Joe Pfeifer & Sandy Diltz)," submitted in opposition to EP 0 957 173 B1 Nov. 30, 2008.

Exhibit entitled "D43: HOSO Sterol Analysis," submitted in opposition to EP 0 957 173 B1 Nov. 30, 2008.
Exhibit entitled "D45: Analysis of Arasco AO17-40-DS oil by silica gel chromatography," submitted in opposition to EP 0 957 173 B1 Nov. 3, 2008.
Exhibit entitled "Determination [of] desmosterol and 24,25-methylenecholest-5-en-3β-ol in high oleic sunflower oil (HOSO)," submitted in opposition to EP 0 957 173 B1 Jul. 3, 2008.
Second declaration by Dr. Higashiyama and third declaration by Dr. Fujikawa submitted in opposition to EP 0 957 173 B1, Jan. 29, 2009.
Opposition to EP 0 957 173 B1, Decision Revoking the European Patent, filed Jun. 6, 2008.
Exhibit entitled "D53: Sterol analysis of oils produced in fermentors using defatted soybean as nitrogen source," submitted in In re EP 0 957 173 B1, Appeal T1540/08-3304, Mar. 23, 2009.
Exhibit entitled "D52: Peak assignment of 24,25-methylenecholest-5-en-3β-ol (24,25M) and ergosta-5,25-dien-3β-ol (egosta-5,25) by means of NMR, GC-FID and GC-MS," submitted in In re EP 0 957 173 B1, Appeal T1540/08-3304, Mar. 23, 2009.
Exhibit entitled "D50: Results of sterol analysis of oils obtained as described in D49," submitted in In re EP 0 957 173 Bl, Appeal T1540/08-3304, Mar. 25, 2009.
Exhibit entitled "D49: Fermentation of ATCC 32222 using soy derived nitrogen at two nitrogen levels and two dissolved oxygen levels," submitted in In re EP 0 957 173 B1, Appeal T1540/08-3304, Mar. 25, 2009.
Declaration by Raymond Michael Gladue, submitted in In re EP 0 957 173 B1, Appeal T1540/08-3304, Mar. 31, 2009.
Letter relating to Appeal Procedure, submitted in in re EP 0 957 173 B1, Appeal T1540/08-3304, Apr. 16, 2011.
Marked OD Decision of Jan. 15, 2010 from In re EP 1 454 990 B1, Appeal T0716/10, pp. 5-7, submitted in In re EP 0 957 173 B1, Appeal T1540/08-3304, Apr. 16, 2011.
Exhibit D56, Collated Data & Graph Annex, submitted in In re EP 0 957 173 B1, Appeal T1540/08-3304, Apr. 16, 2011.
Exhibit D54, Declaration of Nozomu Kamada, submitted in In re EP 0 957 173 B1, Appeal T1540/08-3304, Apr. 16, 2011.
Exhibit D55, Declaration No. 2 of Nozomu Kamada, submitted in In re EP 0 957 173 B1, Appeal T1540/08-3304, Apr. 16, 2011.
Response to further submissions letter of the patent proprietor, submitted in In re EP 0 957 173 B1, Appeal T1540/08-3304, Aug. 5, 2011.
Communication relating to Appeal Procedure, submitted in In re EP 0 957 173 B1, Appeal T1540/08-3304, Aug. 8, 2011.
Exhibit D57 from In re EP 1 454 990 B1, Appeal T0716/10, Declaration of Cindy Panker, submitted in In re EP 0 957 173 B1, Appeal T1540/08-3304, Aug. 8, 2011.
Exhibit D59 from In re EP 1 454 990 B1, Appeal T0716/10, Declaration of Ray Gladue, submitted in In re EP 0 957 173 B1, Appeal T1540/08-3304, Aug. 8, 2011.
Letter dealing with oral proceedings during the appeal procedure and Exhibits D56A, D56B, and D56C, submitted In re EP 0 957 173 B1, Appeal T1540/08-3304, Sep. 11, 2011.
Exhibit D60, Fourth Declaration of Shigeaki Fujikawa (first submitted Sep. 11, 2011, without execution), submitted in In re EP 0 957 173 B1, Appeal T1540/08-3304, Sep. 14, 2011.
Letter dealing with oral proceedings during the appeal procedure, submitted in re EP 0 957 173 B1, Appeal T1540/08-3304, Sep. 11, 2011.
Exhibit D57, graph compositional ratio relative to total sterols, submitted in In re EP 0 957 173 B1, Appeal T1540/08-3304, Sep. 11, 2011.
Exhibit D58, graph compositional ratio relative to desmosterol, submitted in In re EP 0 957 173 B1, Appeal T1540/08-3304, Sep. 11, 2011.
Exhibit D59, graph compositional ratio relative to total sterols with lower limit of 5%, submitted in In re EP 0 957 173 B1, Appeal T1540/08-3304, Sep. 11, 2011.
Letter dealing with oral proceedings during the appeal procedure, submitted In re EP 0 957 173 B1, Appeal T1540/08-3304, Oct. 4, 2011.

(56) References Cited

OTHER PUBLICATIONS

Exhibit D60, Statistical analysis of premise of Suntory with respect to ergosta as submitted by Suntory on Sep. 12, 2011, submitted in In re EP 0 957 173 B1, Appeal T1540/08-3304, Oct. 4, 2011.
Communication of the Board of Appeal, mailed in In re EP 0 957 173 B1, Appeal T1540/08-3304, Oct. 6, 2011.
Minutes of the public oral proceedings before the Technical Board of Appeal 3.3.04 of Oct. 12, 2011, mailed in In re EP 0 957 173 B1, Appeal T1540/08-3304, Oct. 19, 2011.
Decision of the Technical Board of Appeal 3.3.04 of Oct. 12, 2011, mailed in In re EP 0 957 173 B1, Appeal T1540/08-3304, Mar. 7, 2012.
Petitions for Review of Decision No. T1540/08-3.3.04 according to Art 112a EPC, submitted in In re EP 0 957 173 B1, Appeal T1540/08-3304, May 16, 2012.
Communication from the Enlarged Board of Appeal pursuant to Articles 13 and 14(2) RPEBA, mailed in In re EP 0 957 173 B1, Appeal T1540/08-3304, Jan. 25, 2013.
Letter relating to review procedure, submitted in In re EP 0 957 173 B1, Appeal T1540/08-3304, Apr. 3, 2013.
Letter relating to review procedure with Declaration of Gerard Patrick Stoner and Annexes 1-5, submitted in In re EP 0 957 173 B1, Appeal T1540/08-3304, Jul. 16, 2013.
Letter relating to review procedure, submitted in In re EP 0 957 173 B1, Appeal T1540/08-3304, Jul. 17, 2013.
Shimizu et al., "Occurrence of a Novel Sterol, 24,25-Methylenecholest-5-en-3β-ol, in *Mortierella alpine* 1S-4", LIPIDS, vol. 27. No. 6, 1992, pp. 481-483.
Shinmen et al., "Production of arachidonic acid by *Mortierella* fungi", Applied Microbiology and Biotechnology, 1989, vol. 13, pp. 11-16, Springer-Verlag, Berlin, Germany.
Jereonkitmongkol et al., "Production of 5,8,11-cis-Eicosatrienoic acid by 12-Desaturase defective mutant of *Mortierella aphina* 1S-4", J. American Oil Chem Soc., vol. 69, No. 9, pp. 939-944, 1992.
Yoshifumi et al., Chemical Abstracts, Abstract No. 55750, vol. 111, No. 7, 1989.
Declaration of Professor Andrew James Sinclair submitted in opposition to European Patent Application No. 97937813.0, 2005.
Declaration of Assistant Professor Ann Campbell Lawrie submitted in opposition to European Patent Application No. 97937813.0, 2005.
Declaration of Mr. William R. Egbert submitted in opposition to European Patent Application No. 97937813.0, 2005.
Notice of Opposition against EP 0957137 by Martek Biosciences Corporation, 2005.

PROCESS FOR PRODUCING UNSATURATED FATTY ACID-CONTAINING OILS

This is a Continuation of application Ser. No. 09/254,152, filed Feb. 26, 1999, now U.S. Pat. No. 7,091,244, which is a PCT National Stage of PCT/JP97/02989 filed Aug. 27, 1997, which claim priority to Japanese Patent Application No. 8-230210 filed Aug. 30, 1996. Each listed U.S. patent and/or application is incorporated by reference in its entirety.

FIELD OF THE INVENTION

The present invention relates to a process for producing unsaturated fatty acid-containing oils with a low 24,25-methylenecholest-5-en-3β-ol content using microorganisms belonging to the genus *Mortierella*, subgenus *Mortierella*.

RELATED ART

Microorganisms belonging to the genus *Mortierella*, subgenus *Mortierella* are known as microorganisms which produce unsaturated fatty acids such as arachidonic acid, dihomo-γ-linolenic acid and eicosapentaenoic acid, and processes have been developed for efficient production of arachidonic acid, dihomo-γ-linolenic acid and eicosapentaenoic acid by fermentation using these microorganisms Japanese Unexamined Patent Publications No. 63-44891, No. 63-12290, No. 63-14696, No. 5-91887, No. 63-14697). In addition there is also known a process for producing Mead acid using mutant strains having reduced or defective in Δ12 desaturating activity, which are obtained by mutating microorganisms belonging to the genus *Mortierella*, subgenus *Mortierella*(Japanese Unexamined Patent Publication No. 5-91888).

Unsaturated fatty acids such as dihomo-γ-linolenic acid, arachidonic acid, eicosapentaenoic acid and Mead acid are precursors of prostaglandins, thromboxanes, prostacyclins, leucotrienes and the like which have powerful and versatile physiological activity, and much attention is therefore being directed to foods and animal feeds to which these are added.

For example, arachidonic acid is said to be a precursor of prostaglandins, thromboxanes, prostacyclins and leucotrienes which exhibit physiological activity including uterine muscle contracting and relaxing effects, vasodilator and antihypertensive effects, etc., and recently research has been rapidly progressing on docosahexaenoic acid (hereunder also abbreviated to "DHA") as an essential component particularly for infant development.

Specifically, Lanting et al. (LANCET, Vol. 344, 1319-1322 (1994)) have examined infants raised on breast milk and infants raised on infant powdered milk for 3 weeks or more after birth, with follow-up to 9 years of age, studying the incidence of minor damage to cranial nerves from a behavioral perspective, and have reported that the incidence of brain damage in children raised on infant powdered milk is twice that of children raised on breast milk. This shocking result suggests that higher unsaturated fatty acids such as DHA and arachidonic acid which are present in breast milk but virtually absent in infant powdered milk play a role in the development of the brain. Subsequent reports have also shown results suggesting that higher unsaturated fatty acids are connected with the development of the brain and retina.

Nevertheless, while unsaturated fatty acid-containing oils are considered to be highly safe, the issue of their microbial sources has prevented them from wide use throughout the world; meanwhile, in LIPIDS, Vol. 27, No. 6, 481-483(1992), *Mortierella alpina* 1S-4 was reported to produce 24,25-methylenecholest-5-en-3β-ol which to that time was not known to occur naturally. Thus, it has been desired to develop unsaturated fatty acid-containing oils obtained from microorganisms belonging to the genus *Mortierella* subgenus *Mortierella* which can be more safely utilized for foods and animal feeds.

DISCLOSURE OF THE INVENTION

It is therefore an object of the present invention to provide a microorganic oil which can be safely used in foods and animal feeds and which can economically and stably provide unsaturated fatty acids.

In order to solve the problem described above, the present inventors have searched for a process for efficient production of unsaturated fatty acid oils with a low content of 24,25-methylenecholest-5-en-3β-ol the use of which as a food is still unknown, and have studied in detail the relationship between various medium components and sterol compositions; as a result they have completed the present invention upon finding that it is possible to obtain oils with a low compositional ratio of 24,25-methylenecholest-5-en-3β-ol by using a nitrogen source derived from soybean for culturing of microorganisms belonging to the genus *Mortierella* subgenus *Mortierella*.

In other words, the present invention relates to a process for producing unsaturated fatty acid-containing oils, which comprises culturing a microorganism belonging to the genus *Mortierella* subgenus *Mortierella* in a medium containing a nitrogen source derived from soybean, and collecting the unsaturated fatty acid-containing oil from the culture product.

EMBODIMENT FOR CARRYING OUT THE INVENTION

According to the invention, unsaturated fatty acids are fatty acids with at least 16 carbon atoms and at least one double bond, among which higher unsaturated fatty acids are generally fatty acids with at least 1.8 carbon atoms and at least two double bonds, and as examples there may be mentioned γ-linolenic acid, dihomo-γ-linolenic acid, arachidonic acid, eicosapentaenoic acid and Mead acid.

As examples of microorganisms belonging to the genus *Mortierella* subgenus *Mortierella* according to the invention there may be mentioned *Mortierella elongata*, *Mortierella exigua*, *Mortierella hygrophila*, *Mortierella alpina*, etc., and specifically there may be mentioned *Mortierella elongata* IFO8570, *Mortierella exigua* IFO8571, *Mortierella hygrophila* IFO5941, *Mortierella alpina* IFO8568, ATCC16266, ATCC32221, ATCC42430, CBS219.35, CBS224.37, CBS250.53, CBS343.66, CBS527.72, CBS529.72, CBS608.70, CBS754.68 and other cell lines.

These strains are all obtainable without restrictions from the Institute of Fermentation, Osaka (IFO), American Type Culture Collection (ATCC) and Centraalbureau voor Schimmelcultures (CBS). *Mortierella elongata* SAM0219 (FERM P-8703) (FERM-BP 1239) which was isolated from soil by the research group for the present invention, may also be used. These type culture cell lines or naturally occurring isolated cell lines may be used directly, but by growth and/or isolation at least once it is possible to obtain a natural mutant with different properties than the original cell line.

The microorganisms used according to the invention include mutant strains or recombinant strains of microorganisms belonging to the genus *Mortierella* subgenus *Mortierella*(wild strains), i.e. those designed either to give a higher unsaturated fatty acid content in the oil, a higher total oil content, or both, compared to the amount produced by the original wild strain, when cultured using the same substrate.

Also included are microorganisms designed to produce the same amount of unsaturated fatty acid as the wild strain through the efficient use of a substrate with an excellent cost effect. As examples there may be mentioned *Mortierella alpina* SAM1861 (FERM BP-3590) as a mutant strain defective in Δ12 desaturating activity and *Mortierella alpina* SAM1860 (FERM BP-3589) as a mutant strain defective in Δ5 desaturating activity.

The above-mentioned microorganisms belonging to the genus *Mortierella* subgenus *Mortierella* in the form of spores, hypha or a preculture obtained by previous culturing are inoculated into a liquid medium or solid medium and cultured. The carbon source used may be glucose, fructose, xylose, saccharose, maltose, soluble starch, molasses, glycerol, mannitol, citric acid, corn starch or any other conventional one, but glucose, maltose, fructose, corn starch, glycerol and citric acid are particularly preferred.

According to the invention, by using a nutrient source obtained from soybean as the nitrogen source it is possible to lower the compositional ratio of 24,25-methylenecholest-5-en-3β-ol in the oil.

The soybean-derived nitrogen source used for the invention is one with a nitrogen content of at least 2 wt %, preferably at least 3 wt % and more preferably at least 5% with respect to the total components except for water. The soybean-derived nitrogen source may be one or a combination of different types of defatted soybean or soybean subjected to heat treatment; acid treatment; alkali treatment; enzyme treatment; chemical modification; denaturation and/or renaturation by chemical and/or physical processing including heat treatment, acid treatment, alkali treatment, enzyme treatment, chemical modification, etc.; removal of a portion of the components with water and/or organic solvents; removal of a portion of the components by filtration and/or centrifugation; freezing; crushing; drying; sifting; etc., or a product of processing in the same manner as non-defatted soybean; as common candidates there may be mentioned soybean, defatted soybean, soybean flakes, edible soybean protein, okara, soy milk and roasted-soybean flour (kinako), among which are particularly preferred heat-denatured defatted soybean, and especially heat-denatured defatted soybean from which the ethanol-soluble components have been further removed.

When necessary one or more different additional nitrogen sources may also be added so long as the sterol composition is not notably affected, and examples include organic nitrogen sources such as peptone, yeast extract, malt extract, meat extract, casaminic acid, corn steep liquor and urea, and inorganic nitrogen sources such as sodium nitrate, ammonium nitrate and ammonium sulfate.

Also, when necessary trace nutrient sources may be used, including inorganic salts such as potassium phosphate, potassium dihydrogen phosphate and other phosphate salts, ammonium sulfate, sodium sulfate, magnesium sulfate, iron sulfate, copper sulfate, magnesium chloride, calcium chloride, etc. and vitamins.

According to the invention, accumulation of the unsaturated fatty acid of interest may be accelerated by accomplishing the culturing with addition of a substrate for the unsaturated fatty acid in the medium. The unsaturated fatty acid substrate used may be, for example, a hydrocarbon such as hexadecane or octadecane; a fatty acid such as oleic acid or linolic acid or a salt, for example a sodium or potassium salt thereof, or a fatty acid ester such as an ethyl ester, glycerol fatty acid ester or sorbitan fatty acid ester; or an oil such as olive oil, soybean oil, rapeseed oil, cottonseed oil or coconut oil, and these may be used alone or in combinations. The total amount of the substrate added is 0.001 to 10 wt %, and preferably 0.5 to 10 wt %, with respect to the medium. Any of these substrates may also be used as the sole carbon source for culturing.

The above-mentioned carbon sources, nitrogen sources, inorganic salts, vitamins and/or additives may be added to the medium prior to the start of culturing or to the culture broth during the cultivation. The medium components can be added all at once, or continuously or periodically through a few additions. The medium components may each be added alone or as a mixture. There are no particular restrictions on the concentrations of the medium components so long as growth of the cells is not inhibited. In practical usage, the carbon source should be at a concentration of 0.1 to 30 wt %, preferably 1 to 15 wt %, and the nitrogen source should be at a concentration of 0.01 to 10 wt %, and preferably 0.1 to 5 wt %.

The culturing temperature is 5 to 40° C., and preferably 20 to 30° C., and the unsaturated fatty acid may also be produced by growth of the cells by culturing at 20 to 30° C. followed by continued culturing at 5 to 20° C. This manner of temperature control may also be employed to increase the yield of higher unsaturated fatty acids content in the fatty acids which are produced. The pH of the medium is 4 to 10, and preferably 5 to 8, and culturing with aeration and agitation, shake culturing or static culturing may be employed. The culturing is normally carried out for 2 to 20 days, preferably 5 to 20 days, and more preferably 5 to 15 days.

A fermenter, especially culturing fermenter with aeration and agitation or air-lift culturing fermenter may be used for submerged culturing with aeration to enable production with yields suited for unsaturated fatty acid-containing oils as commercial products. In such cases, the unsaturated fatty acid-containing oil can be even more efficiently produced by maintenance during the culturing to a glucose concentration of at least 0.3 wt % and/or an average glucose concentration of at least 0.5 wt %, preferably a glucose concentration of at least 0.5 wt % and/or an average glucose concentration of at least 0.7 wt %, and more preferably a glucose concentration of 0.5-5 wt % and/or an average glucose concentration of 0.7-3 wt %, for at least 3 days after the start of culturing. For example, arachidonic acid can be produced at 100 mg or more, and preferably 120 mg or more to one gram of dry cells.

Thus, an oil which is rich in the desired unsaturated fatty acid and low in 24,25-methylenecholest-5-en-3β-ol, is accumulated in large quantities in the cells.

The desired oil can be obtained according to a conventional method from the culture broth taken during production of the oil by the cell culturing or after its sterilization, the culture broth obtained at the end of culturing or after its sterilization, or the cultured cells collected from either, alternatively in dry form.

The desired oil may be collected from the cultured cells by the following method, for example.

After culturing is complete, the cultured cells are obtained from the culture broth by a conventional solid/liquid separation means such as centrifugation and/or filtration. The cultured cells are preferably washed, disrupted and dried. The drying may be accomplished by freeze drying, air drying or the like. The dry cells are preferably subjected to extraction with an organic solvent preferably under a nitrogen stream. The organic solvent used may be ether, hexane, methanol, ethanol, chloroform, dichloromethane, petroleum ether or the like, and satisfactory results can also be obtained by alternate extraction with methanol and petroleum ether or by extraction using a chloroform-methanol-water monolayer system.

By removing the organic solvent from the extract under reduced pressure, it is possible to obtain an unsaturated fatty acid-containing oil at a high concentration. The extraction may also be accomplished using wet cells, instead of by the method described above. In this case there is used a water-compatible solvent such as methanol or ethanol, or a water-compatible mixed solvent including one of these with water and/or another solvent. The other procedures are the same as described above.

The oil obtained in this manner contains the unsaturated fatty acids in a state of triglycerides and phosphatidylcholine, phosphatidylethanolamine or phosphatidylinositol, but most of it is in the form of triglycerides. In order to separate and purify the unsaturated fatty acid-containing triglycerides from the unsaturated fatty acid-containing oil collected from the cultured product, a conventional method may be used for hexane extraction followed by deacidification, decoloration, deodorization and degumming treatment, or cooling separation.

According to the invention, the compositional ratio of 24,25-methylenecholest-5-en-3β-ol is determined by the following method based on sterol composition analysis.

The sterol composition analysis will be explained first. A 30 to 80 mg portion of the oil is weighed out into a test tube with stopper, 4 mL of methanol and 1 mL of a 33% aqueous potassium hydroxide solution are added, and the stopper is fitted. After reaction for one hour while gently stirring at 80° C., the mixture is allowed to be cooled and the oil-soluble components are extracted with hexane. The resulting hexane solution is washed with water until a phenolphthalein indicator does not color the aqueous layer, and is then concentrated under a reduced pressure to obtain an analytical sample. The analytical sample is dissolved in a small amount of hexane and subjected to gas chromatography under the conditions listed in the table given below. By comparing the gas chromatogram with a commercially available desmosterol standard, the desmosterol peaks are identified.

The components which are detected within 0.8 to 2.0 times the retention time of desmosterol are the sterol components, and the peak areas of the gas chromatograms for all of the sterol components within the retention time are determined by a conventional method. The ratio of the peak area of each component to the sum of the total peak areas of the components is taken as the compositional ratio of each component. For example, the ratio of the peak area detected for desmosterol with respect to the sum of the total sterol area is the compositional ratio of desmosterol. 24,25-methylenecholest-5-en-3β-ol is detected in a retention time of 1.07 to 1.12 times the retention time of desmosterol. The ratio of the peak area detected for 24,25-methylenecholest-5-en-3β-ol with respect to the sum of all the peak areas is the compositional ratio of 24,25-methylenecholest-5-en-3β-ol.

Column used: ULBON HR-1 (inner diameter: 0.25 mm, length: 25 m)
Column temperature: 280° C.
Inlet and detector temperature: 300° C.
Carrier gas and gauge pressure, helium: 1.2 kg/cm$^2$
Make-up gas and flow rate, nitrogen: 70 mL/minute
Detector: FID
Split ratio: 20

The unsaturated fatty acid-containing oil of the invention has a 24,25-methylenecholest-5-en-3β-ol compositional ratio of 35% or less, preferably 33% or less, and more preferably 30% or less, and/or the 24,25-methylenecholest-5-en-3β-ol proportion is 1.2 or lower, preferably 0.9 or lower and more preferably 0.6 or lower with respect to the desmosterol present in the oil. Desmosterol is a component included with 24,25-methylenecholest-5-en-3β-ol in oils obtained by culturing microorganisms belonging to the genus *Mortierella* subgenus *Mortierella*, and it is known to be present in breast milk.

As an example of an unsaturated fatty acid-containing oil according to the invention there may be mentioned an arachidonic acid-containing oil with 20 to 54 wt % and preferably 30 to 50 wt % arachidonic acid with respect to the total fatty acids in the oil, and a 24,25-methylenecholest-5-en-3β-ol compositional ratio of 35% or lower, preferably 33% or lower and more preferably 30% or lower and/or a 24,25-methylenecholest-5-en-3β-ol proportion of 1.2 or lower, preferably 0.9 or lower and more preferably 0.6 or lower with respect to the desmosterol present in the oil.

The oil properties of the arachidonic acid containing oil are such that the triglyceride content is 90% or greater, the moisture content is 0.1% or lower, the acid value is 0.5 or lower and the peroxide value is 5 or lower, while the color is ≤50 yellow and ≤10 by the Lovibond method in a 133.4 mm cell, and the fatty acid composition is 20 to 54%, with preferably 30 to 50% arachidonic acid, 0.2 to 0.7% myristic acid, 10 to 16% palmitic acid, 4 to 10% stearic acid, 5 to 15% oleic acid, 5 to 15% linolic acid, 1 to 5% γ-linolenic acid, 0.1 to 2% α-linolenic acid, 1 to 6% dihomo-γ-linolenic acid, 0 to 1% eicosapentoenoic acid and 2 to 7% lignoceric acid.

The oil is rich in the triglyceride form of arachidonic acid, and either contains no eicosapentoenoic acid or contains it only in a very trace amount, and is therefore desirable as a material for foods, and especially immature infant formula, infant formula, baby food and pregnancy food. The unsaturated fatty acid-containing oil of the invention can also be safely used in foods and animal feeds because of its low content of 24,25-methylenecholest-5-en-3β-ol, the edibility of which has not yet been established.

EXAMPLES

The present invention will now be explained in more detail by way of examples.

Example 1

Using *Mortierella elongata* IFO8570 as the arachidonic acid-producing cell line, 1400 L of a medium containing 2% glucose, 1% edible soybean protein trade name: Esusan Meat, product of Ajinomoto Co.) and 0.1% rapeseed oil was placed in a 2000 L fermenter equipped with an agitator and aerator and culturing with aeration and agitation was initiated under conditions of 28° C. temperature, 1.0 vvm aeration 80 rpm agitation and 1.0 kg/cm$^2$G headspace pressure. The glucose concentration was kept at 1.5% by feeding glucose, and after culturing for 7 days the cells were recovered by filtration and subjected to oil extraction. As a comparative example, culturing and oil extraction were carried out in the same manner using 1% yeast extract instead of the edible soybean protein.

Upon analyzing the sterol composition of the resulting oil according to the procedure described above, desmosterol was detected at a retention time of about 9.6 minutes and 24,25-methylenecholest-5-en-3β-ol was detected at a retention time of about 10.5 minutes. In the comparative example, desmosterol was detected at a retention time of about 6.5 minutes and 24,25-methylenecholest-5-en-3β-ol was detected at a retention time of about 7.2 minutes. The results are shown in Table 1. Thus, an arachidonic acid-containing oil was obtained with a low compositional ratio of 24,25-methylenecholest-5-en-3β-ol.

TABLE 1

|  | 24,25-methylene cholest-5-en-3β-ol compositional ratio (A) | Desmosterol compositional ratio (B) | A/B | Total sterol content* | Arachidonic acid content** |
|---|---|---|---|---|---|
| Example | 30% | 65% | 0.46 | 1% | 8% |
| Comp. Example | 65% | 27% | 2.41 | 1% | 9% |

*Sterol content in oil
**Arachidonic acid content with respect to total fatty acids in oil Example 2

*Mortierella alpina* CBS754.68 was used as the arachidonic acid-producing cell line, and 600 L of a medium containing 4% glucose, 1.3% roasted soybean flour (kinako), 0.2% yeast extract and 0.1% olive oil was placed in a 1000 L fermenter equipped with an agitator and aerator, for culturing with aeration and agitation for 5 days under conditions of 24° C. temperature, 1.0 vvm aeration, 100 rpm agitation and 0.5 kg/cm$^2$G headspace pressure, followed by filtration and drying to recover the cells and hexane extraction to obtain an oil. As a comparative example, culturing was carried out in the same manner using a medium of 4% glucose, 1.5% yeast extract and 0.1% olive oil to obtain an oil. In both the example and the comparative example, 1% glucose was added on the 2nd day of culturing.

Upon analyzing the sterol composition of the resulting oil according to the procedure described above, desmosterol was detected at a retention time of about 10.2 minutes and 24,25-methylenecholest-5-en-3β-ol was detected at a retention time of about 11.2 minutes. In the comparative example, desmosterol was detected at a retention time of about 6.4 minutes and 24,25-methylenecholest-5-en-3β-ol was detected at a retention time of about 7.1 minutes. The results are shown in Table 2. Thus, an arachidonic acid-containing oil was obtained with a low compositional ratio of 24,25-methylenecholest-5-en-3β-ol.

TABLE 2

|  | 24,25-methylene cholest-5-en-3β-ol compositional ratio (A) | Desmosterol compositional ratio (B) | A/B | Total sterol content* | Arachidonic acid content** |
|---|---|---|---|---|---|
| Example | 25% | 53% | 0.47 | 1.2% | 48% |
| Comp. Example | 68% | 16% | 4.25 | 1.1% | 46% |

*Sterol content in oil
**Arachidonic acid content with respect to total fatty acids in oil Example 3

*Mortierella alpina* ATCC32221 and *Mortierella alpina* ATCC42430 were used as arachidonic acid-producing cell lines, and each was cultured. After placing 25 L of a medium containing 4% glucose, 1.2% defatted soy powder, 0.2% potassium hydrogen phosphate and 0.1% soybean oil in a 50 L fermenter equipped with an agitator and aerator, culturing with aeration and agitation was carried out for 5 days under conditions of 28° C. temperature, 1.0 vvm aeration, 300 rpm agitation and 1.0 kg/cm$^2$G headspace pressure, followed by filtration and drying to recover the cells and hexane extraction to obtain an oil from the recovered cells.

As a comparative example, culturing was carried out in the same manner using a medium of 4% glucose, 1.2% beer yeast powder, 0.2% potassium hydrogen phosphate and 0.1% rapeseed oil to obtain an oil. In both the example and the comparative example, 1% glucose was added on the 2nd day of culturing. The sterol composition of the resulting oil was analyzed according to the procedure described above. The results are shown in Table 3. Thus, an arachidonic acid-containing oil was obtained with a low compositional ratio of 24,25-methylenecholest-5-en-3β-ol.

TABLE 3

|  | 24,25-methylene cholest-5-en-3β-ol compositional ratio (A) | Desmosterol compositional ratio (B) | A/B | Total sterol content* | Arachidonic acid content** |
|---|---|---|---|---|---|
| *Mortierella alpina* ATCC32221 | 5% | 67% | 0.07 | 0.9% | 25% |
| Comp. Example | 37% | 28% | 1.32 | 0.8% | 20% |
| *Mortierella alpina* ATCC42430 | 5% | 35% | 0.14 | 0.9% | 18% |
| Comp. Example | 40% | 25% | 1.60 | 1.0% | 18% |

*Sterol content in oil
**Arachidonic acid content with respect to total fatty acids in oil Example 4

Using *Mortierella alpina* CBS754.68 as the arachidonic acid-producing cell line, 1400 L of a medium containing 2% glucose, 1.5% soybean protein and 0.1% soybean oil was placed in a 2000 L fermenter equipped with an agitation and aeration, and culturing with aeration and agitation was initiated under conditions of 24° C. temperature, 1 vvm aeration, 80 rpm agitation and 200 kPa headspace pressure. The glucose concentration was kept at 0.5 to 1.5% by feeding glucose, and after culturing for 7 days the cells were recovered by filtration. After drying the cells, they were extracted with hexane, the extracted oil was subjected to deacidification, decoloration and deodoration, and 0.05% tocopherol was added as an antioxidant. The resulting oil was analyzed and found to have the following composition.
Analysis results
Triglyceride content: 95.6%
Moisture: 0.04%
Acid value: 0.08
Peroxide value: 2.16
Color (Lovibond method, 133.4 mm cell): yellow: 20.1, red: 1.4
Fatty acid composition:

| | |
|---|---|
| arachidonic acid | 44.4% |
| myristic acid | 0.6% |
| palmitic acid | 14.6% |
| stearic acid | 8.8% |
| oleic acid | 6.3% |
| linolic acid | 10.2% |
| γ-linolenic acid | 3.2% |

-continued

| | |
|---|---|
| α-linolenic acid | 0.8% |
| dihomo-γ-linolenic acid | 5.2% |
| eicosapentoenoic acid | 0.2% |
| lignoceric acid | 4.8% |

Total sterol content: 1.0%
24,25-methylenecholest-5-en-3β-ol compositional ratio: 24%
Desmosterol compositional ratio: 67%

Example 5

The arachidonic acid-containing oil obtained in Example 4 was appropriately mixed with fish oil and vegetable oil to obtain an essential fatty acid-adjusted oil. In addition to the essential fatty acid-adjusted oil the raw materials and components listed below were prepared for formulation of 100 kg of powdered infant formula. After dissolving, mixing and refining the raw materials according to conventional methods, they were sterilized, concentrated and homogenized, and then spray dried to obtain powdered infant formula.

| Raw materials and components | |
|---|---|
| casein | 5.6 kg |
| whey protein concentrate | 24.0 kg |
| essential fatty acid-adjusted oil (composed mainly of linolic acid, α-linolenic acid) | 25.0 kg |
| arachidonic acid content | 80 g |
| docosahexaenoic acid content | 25 g |
| eicosapentaenoic acid content | 10 g |
| saccharides (lactose and oligosaccharides) | 43.4 kg |
| minerals and vitamins | 2 kg |
| TOTAL | 100 kg |

The invention claimed is:

1. A process for producing an unsaturated fatty acid-containing oil comprising:
(a) culturing a microorganism belonging to the genus *Mortierella* subgenus *Mortierella* in a liquid medium containing a nitrogen source derived from soybean in a fermenter, wherein the ratio of the nitrogen source derived from soybean with respect to the total nitrogen source in the medium is at least 86%, and
(b) collecting the unsaturated fatty acid-containing oil from the cultured product,
wherein the unsaturated fatty acid-containing oil has a 24,25-methylenecholest-5-en-3β-ol compositional ratio of 35% or lower, a 24,25-methylenecholest-5-en-3β-ol compositional ratio in a proportion of 1.2 or less with respect to the desmosterol compositional ratio, and an arachidonic acid content of 30 to 50%, and wherein the culture step is carried out while maintaining i) a glucose concentration within the range of 0.5 to 5 wt % during the first 3 days of culturing, and/or ii) an average glucose concentration within the range of 0.7 to 3 wt % during the first 3 days of culturing.

2. The process of claim 1, wherein said nitrogen source derived from soybean has a nitrogen content of at least 2 wt % with respect to the total components except for water.

3. The process of claim 1, wherein said nitrogen source derived from soybean is from defatted soybean subjected at least to heat denaturation.

4. The process of claim 1, wherein said cultured product is (a) culture broth taken during production of the oil by the cultured microorganisms or after sterilization of the culture broth, (b) culture broth obtained at the end of culturing or after sterilization of the culture broth, (c) the cultured microorganisms collected from either (a) or (b), or (d) a dry form of the cultured product.

5. The process of claim 1, wherein said fermentor is a fermentor equipped with agitator and air sparger or an air-lift fermentor.

6. The process of claim 1, wherein the culturing step is carried out for 3 to 20 days.

\* \* \* \* \*